United States Patent
Pituch

(10) Patent No.: US 11,992,330 B2
(45) Date of Patent: *May 28, 2024

(54) SYSTEMS AND METHODS FOR PREVENTING SLEEP DISTURBANCE

(71) Applicant: Daniel W. Pituch, Presto, PA (US)

(72) Inventor: Daniel W. Pituch, Presto, PA (US)

( * ) Notice: Subject to any disclaimer, the term of this patent is extended or adjusted under 35 U.S.C. 154(b) by 45 days.

This patent is subject to a terminal disclaimer.

(21) Appl. No.: 17/490,669

(22) Filed: Sep. 30, 2021

(65) Prior Publication Data
US 2022/0015694 A1    Jan. 20, 2022

Related U.S. Application Data

(63) Continuation of application No. 15/612,382, filed on Jun. 2, 2017, now Pat. No. 11,134,887.

(51) Int. Cl.
*A61B 5/00* (2006.01)
*A61B 5/291* (2021.01)

(52) U.S. Cl.
CPC .......... *A61B 5/4809* (2013.01); *A61B 5/0006* (2013.01); *A61B 5/291* (2021.01); *A61B 5/4818* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 5,534,851 A | 7/1996 | Russek | |
| 5,689,241 A | 11/1997 | Clarke, Sr. et al. | |
| 5,813,993 A | 9/1998 | Kaplan et al. | |
| 5,844,488 A | 12/1998 | Musick | |
| 6,160,478 A | 12/2000 | Jacobsen et al. | |
| 6,167,298 A | 12/2000 | Levin | |
| 6,392,550 B1 | 5/2002 | Najor | |

(Continued)

FOREIGN PATENT DOCUMENTS

WO    2014107795 A1    7/2014

OTHER PUBLICATIONS

General Sleep Corporation, Patient Guide Zmachine Insight & Insight+ Model: DT-200, 2016, 23 pp.

(Continued)

*Primary Examiner* — Etsub D Berhanu
(74) *Attorney, Agent, or Firm* — The Webb Law Firm

(57) ABSTRACT

A sleep monitoring and disturbance mitigation system may include a sleep status monitoring apparatus configured to collect real-time sleep data from a subject; to determine a sleep status based at least partially on the sleep data; and to transmit the real-time sleep data and sleep status to a remote receiving station; and a remote receiving station configured to receive the real-time sleep status data and the sleep status from the sleep status monitoring apparatus; to generate, based at least partially on the real-time sleep data and sleep status, a sleep disturbance priority and a sleep disturbance message including data indicative of the sleep status and the sleep disturbance priority; and to display the sleep disturbance priority message on a display located remotely from the sleep status monitoring apparatus. The sleep status monitoring apparatus may be configured to wirelessly transmit the real-time sleep data and sleep status. Real-time sleep data may include EEG data.

18 Claims, 5 Drawing Sheets

(56) References Cited

U.S. PATENT DOCUMENTS

| | | |
|---|---|---|
| 6,791,462 B2 | 9/2004 | Choi |
| 7,654,948 B2 | 2/2010 | Kaplan et al. |
| 7,868,757 B2 | 1/2011 | Radivojevic et al. |
| 8,089,283 B2 | 1/2012 | Kaplan et al. |
| 8,512,221 B2 | 8/2013 | Kaplan et al. |
| 8,781,568 B2 | 7/2014 | Dugan et al. |
| 8,784,324 B2 | 7/2014 | Heneghan et al. |
| 2006/0019224 A1 | 1/2006 | Behar et al. |
| 2006/0241708 A1 | 10/2006 | Boute |
| 2007/0229249 A1 | 10/2007 | McNeal et al. |
| 2007/0249952 A1 | 10/2007 | Rubin et al. |
| 2008/0139892 A1 | 6/2008 | Juan |
| 2009/0105785 A1 | 4/2009 | Wei et al. |
| 2009/0273467 A1 | 11/2009 | Elixmann et al. |
| 2011/0230790 A1 | 9/2011 | Kozlov |
| 2011/0275960 A1 | 11/2011 | Westerink et al. |
| 2013/0018284 A1 | 1/2013 | Kahn et al. |
| 2014/0347265 A1 | 11/2014 | Aimone et al. |
| 2015/0094544 A1 | 4/2015 | Spolin et al. |
| 2015/0116112 A1 | 4/2015 | Flinsenberg et al. |
| 2015/0141770 A1 | 5/2015 | Rastogi et al. |
| 2015/0199010 A1 | 7/2015 | Coleman et al. |
| 2015/0297109 A1 | 10/2015 | Garten et al. |
| 2016/0066808 A1 | 3/2016 | Hijazi |

OTHER PUBLICATIONS

General Sleep Corporation, Zmachine Insight & Insight+ Model: DT-200 Clinician Instruction and Service Manual Rev. 1.6, 2016, 44 pp.
General Sleep Corporation, Zmachine Synergy Clinician Instruction and Service Manual Version 1.2, 2017, 29 pp.
General Sleep Corporation, Zmachine Synergy Patient Guide Version 1.4, 2017, 23 pp.
Muse: Meditation Made Easy, Muse the brain sensing headband, 2017, http://www.choosemuse.com/.
Singer, "Rewriting Life: Device Tracks How You're Sleeping", MIT Technology Review, 2009, http://www.technologyreview.com/s/414509/device-tracks-how-youre-sleeping/.

SYSTEMS AND METHODS FOR PREVENTING SLEEP DISTURBANCE

CROSS REFERENCE TO RELATED APPLICATIONS

This application is a continuation of U.S. patent application Ser. No. 15/612,382, filed Jun. 2, 2017, which is incorporated herein by reference in its entirety.

BACKGROUND OF THE INVENTION

Field of the Invention

The present invention is directed generally to the field of sleep monitoring, and, more particularly, to systems and methods to minimize disturbance of sleep of a subject by monitoring sleep and conveying disturbance events that are authorized to be administered to the subject.

Description of Related Art

Sleep is important and plays a vital role in good health and well-being. Sleep can affect mental health, physical health, quality of life, and safety. It affects the way individuals act and perform when they are awake. The dangers of sleep deficiency can include physical harm, such as causing accidents while operating vehicles or machinery, or, over time, can cause chronic health problems. Studies have also shown that sleep helps significantly in the healing process. However, in many settings, such as hospitals and nursing homes, individuals who are most in need of sleep are unable to obtain quality sleep. This is due to the numerous disturbances that occur in such settings, such as hospital alarms, medication administration, vital measurements, and other disturbances that occur near constant to those trying to recover. This is sometimes due to emergency scenarios, but often it occurs because personnel tasked with taking care of individuals in such situations often do not consider a patient's sleep schedule and the importance of quality sleep. At least one study has shown that in a hospital setting, over the course of an entire week, most patients never obtain a full sleep cycle, which is typically considered to be 90 minutes.

Devices exist, which are capable of monitoring sleep, such as those disclosed in U.S. Pat. No. 8,512,221 to Kaplan et al., but no such systems have been previously used in combination with other components so as to convey permitted or redistricted disturbance events or protocols to be administered to a subject so as to allow the healing properties of sleep to inure to the benefit of a subject or patient.

SUMMARY OF THE INVENTION

An embodiment of sleep monitoring and disturbance mitigation systems may include a sleep status monitoring apparatus configured to collect real-time sleep data from a subject to determine a sleep status based at least partially on the sleep data; and to transmit the real-time sleep data and sleep status to a remote receiving station; and a remote receiving station configured to receive the real-time sleep status data and the sleep status from the sleep status monitoring apparatus; to generate, based at least partially on the real-time sleep data and sleep status, a sleep disturbance priority and a sleep disturbance message comprising data indicative of the sleep status and the sleep disturbance priority; and to display the sleep disturbance priority message on a display located remotely from the sleep status monitoring apparatus. The sleep status monitoring apparatus may be configured to wirelessly transmit the real-time sleep data and sleep status to the remote receiving station, and the remote receiving station is configured to wirelessly receive the real-time sleep status data and sleep status. The remote receiving station may be configured to generate the sleep disturbance priority and sleep disturbance message based on at least sleep time of the subject. The remote receiving station may be configured to generate the sleep disturbance priority based further on a priority ranking of disturbance events. The priority ranking may include at least two levels of disturbance priority. It may also include at least three levels of disturbance priority.

In some embodiments, the remote receiving station may be configured to generate a sleep disturbance message comprising data capable of conveying at least one of the user actions of: (a) do not disturb the subject except for top priority disturbance events; (b) disturb subject only for intermediate priority disturbance events; and (c) subject is awake and all disturbance events permitted. In such embodiments as well, the remote receiving station may be configured to generate the sleep disturbance level based at least on sleep time of the subject and/or to generate the sleep disturbance priority based further on a priority ranking of disturbance events, where the priority ranking could include at least two and/or three levels of disturbance priority. In some embodiments, the user action (a) do not disturb the subject except for top priority events may be conveyed by a red indicator; the user action (c) subject is awake and all disturbances permitted may be conveyed by a green indicator; and/or the user action (b) disturb subject only for intermediate priority disturbance events may be conveyed by a yellow indicator.

In yet other embodiments, an EEG monitoring sensor may be in communication with the sleep status monitoring apparatus, and the real-time sleep data may be EEG data. The EEG monitoring sensor comprises at least one electrode. The at least one electrode or electrodes may be non-invasive.

In some embodiments, the remote receiving station may be located on or proximate to a subject room doorway or it may be located at an attendant's station positioned remotely from the subject. In some embodiments, the remote receiving station may be a workstation computer, or, alternatively, it may be a mobile communication device, such as a smart phone, tablet computer, or smart watch.

In one embodiment, the system may include an EEG monitoring sensor in communication with the sleep status monitoring apparatus, wherein the real-time sleep data comprises EEG data, wherein the remote receiving station and the display are located on or proximate to a subject room doorway, and wherein the sleep status monitoring apparatus is configured to wirelessly transmit the real-time sleep data to the remote receiving station, and the remote receiving station is configured to wirelessly receive the real-time sleep data, the remote receiving station being configured to generate a sleep disturbance message comprising data capable of conveying at least the user actions of: (a) do not disturb the subject except for top priority disturbance events by generating a red indicator; and (b) subject is awake and all disturbance events permitted by generating a green indicator.

In yet a further embodiment, a sleep monitoring and disturbance mitigation system, including a sleep status monitoring apparatus and a remote receiving station, may include instructions that, when executed, perform the following steps: collect real-time sleep data from a subject at the sleep status monitoring apparatus; determine a sleep status; transmit the real-time sleep data to the remote receiving station; receive the real-time sleep data from the sleep status monitoring at the remote receiving station; generate based at least partially on the real-time sleep data a sleep disturbance priority and a sleep disturbance message comprising data indicative of the sleep disturbance priority; and display the sleep disturbance message on a display located remotely from the sleep status monitoring apparatus. The transmitting of the real-time sleep data to the remote receiving station and receiving of the real-time sleep data at the remote receiving station may include wirelessly transmitting the real-time sleep status data to the remote receiving station and wirelessly receiving the real-time sleep status data at the remote receiving station. The generating of the sleep disturbance message may include generating a message comprising data capable of conveying at least one of the user actions of: (a) do not disturb the subject except for top priority disturbance events; (b) disturb subject only for intermediate priority disturbance events; and (c) subject is awake and all disturbance events permitted. Conveying the user action (a) do not disturb the subject except for top priority events may include a red indicator. Conveying the user action (c) subject is awake and all disturbances permitted may be indicated by a green indicator. The generating of the sleep disturbance level may include generating the sleep disturbance priority based on at least sleep time of the subject. The generating of the sleep disturbance priority may include generating the sleep disturbance priority based further on a priority ranking of disturbance events. As in other embodiments, the priority ranking may include at least two levels of disturbance priority and/or three levels of disturbance priority. Displaying the sleep disturbance message may include displaying on a display located on or proximate to a subject room doorway.

DESCRIPTION OF THE INVENTION

Figure 1:
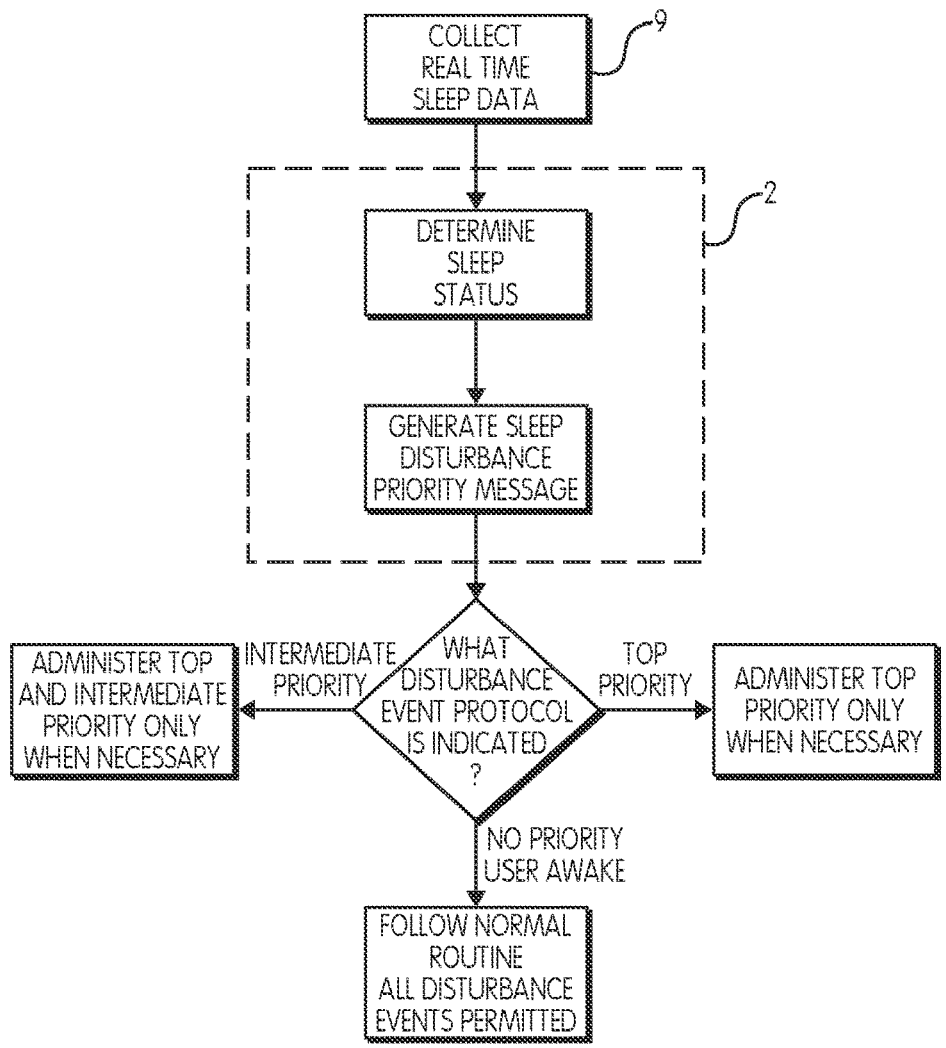
FIG. 1 is a flowchart illustrating an overview of an embodiment of a method to be performed in accordance with a system for preventing sleep disturbance according to the present invention.

With reference to FIG. 1, the system and methods of the presently described embodiment generally may require the following: collecting real time sleep data, determining sleep status, such as the amount of time a subject has been asleep, generating a sleep disturbance priority message, and then administering the protocol dictated by the determined sleep status. The protocol could take the form of performing any number of procedures on a subject individual. As discussed herein, such protocols refer to what the present disclosure will refer to generally as disturbance events. Disturbance events are simply actions or procedures administered to or for a subject, for example, a patient in a hospital setting. Examples of such actions may include taking vital measurements, administering medication, flushing IV fluids, or changing sheets. The systems and methods described herein are described generally in reference to a patient-hospital setting but may take the form of any setting wherein a subject may require periods of continuous and prolonged sleep without disturbance.

Figure 7:
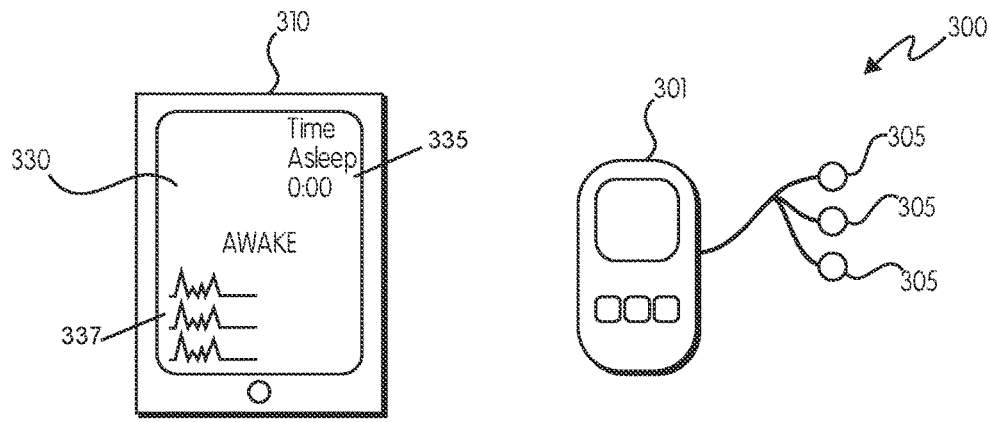
FIG. 7 is a diagrammatical representation of another embodiment of a system for preventing sleep disturbance according to the present invention.

The collection of sleep data can take many forms, and, may, for example, take the form of a sleep monitoring device. One form of a sleep monitoring device that may be used is an electroencephalography (EEG) monitor, which could monitor brain activity. An example of a monitoring device 300 that may be used according to embodiments of the present invention is shown in FIG. 7 and will be described in more detail herein below. Other potential monitoring techniques may include electromyography (EMG), peripheral arterial tone (PAT), systolic upstroke time, electrocardiography (ECG/EKG), electrooculography (EOG), oximetry, heart rate monitoring, such as heart rate variations or heart rhythm variations, actigraphy, galvanic skin response (GSR), respiratory monitoring, eye movements, temperature measurement, motion measurement, such as through accelerometers, or any other type of measurement that can be used to determine and/or measure sleep.

Figure 2:
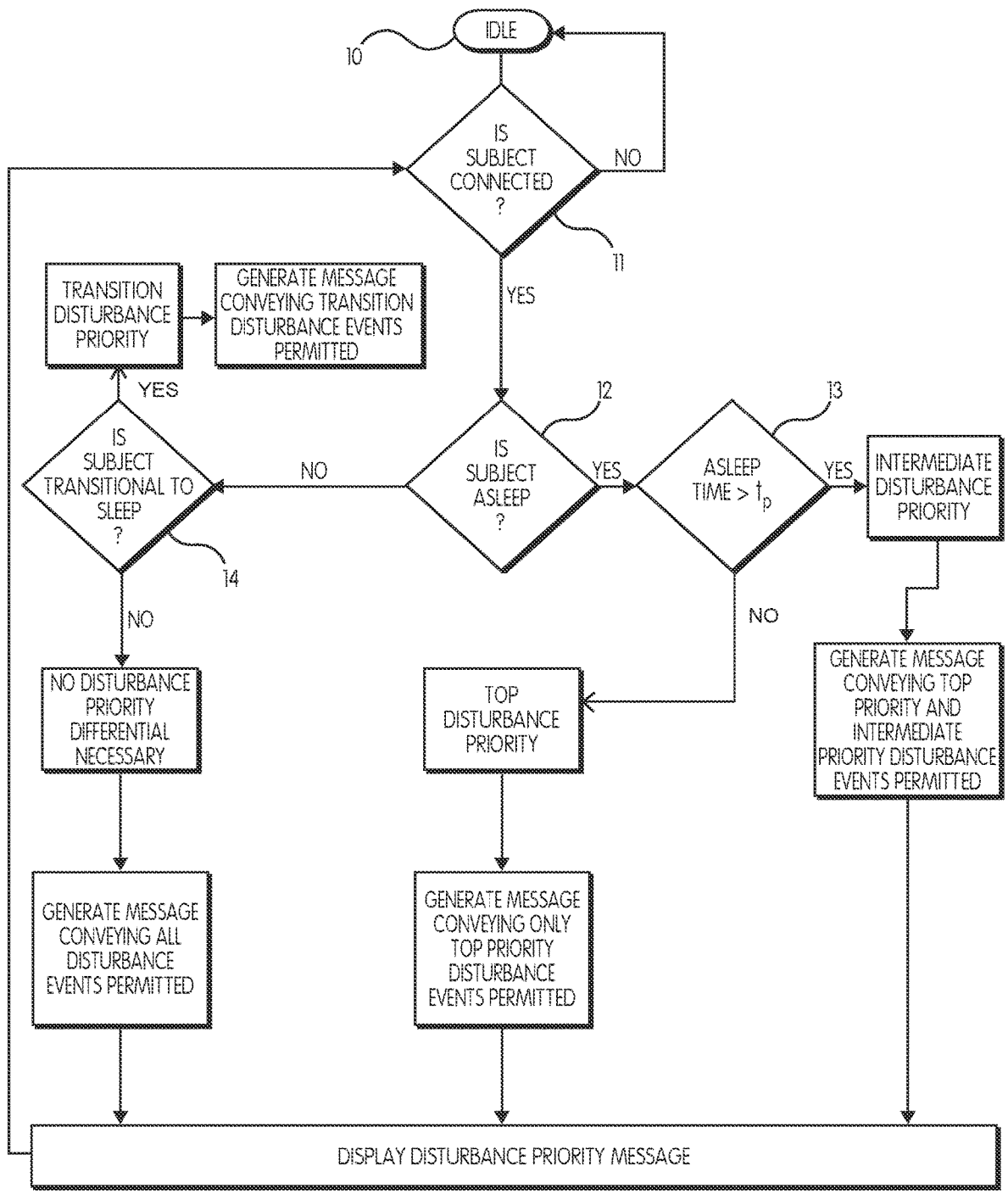
FIG. 2 is a flowchart illustrating an embodiment of the functions highlighted in box 2 of FIG. 1.

The functions included with box 2 of FIG. 1 generally may follow the process detailed at FIG. 2. For example, a monitoring apparatus 101, see, e.g., FIG. 3, may idle if it is determined that the subject is not connected. If the subject is connected to the monitoring device 101, as illustrated at decision point 11, the system may then make a determination of whether the subject is asleep, as indicated by decision point 12 in FIG. 2. This decision may be made at a monitoring apparatus 101, at a receiving station 110, described in more detail herein below, or elsewhere in the overall system. If the subject is asleep, the system may make a sleep status determination, such as at decision point 13. For example, the system may determine for how long the subject has been asleep, what stage of sleep the subject is presently in, or some other measurement of the length and/or quality of the subject's sleep. The example illustrated in FIG. 2 shows an embodiment of the system that uses the amount of time the subject has been asleep to determine what protocol should be used.

In the embodiment of FIG. 2, the system determines whether the subject has been asleep for a predetermined period of time $t_p$. If the subject has, in fact, been asleep for the period of time $t_p$, then an intermediate disturbance priority exists and disturbance events categorized as intermediate priority disturbance events are authorized to be performed. Likewise, as illustrated in FIG. 2, if the system determines that the subject has not been asleep for the predetermined period of time $t_p$, then the subject is in the top disturbance priority category, wherein only disturbance events categorized as top priority disturbance events are authorized to be performed. If it is determined that the subject is awake, indicated in FIG. 2 by the "No" branch of decision point 12, then the system may determine at decision point 14 whether the subject is transitioning to sleep, such as by one or any combination of the sleep monitoring techniques described above. If it is determined that the subject is transitioning to sleep, indicated by the "Yes" branch of decision point 14, then disturbance events authorized only for the transition phase of sleep may be administered to the subject. If it is determined that the subject is not transitioning to sleep, indicated by the "No" decision branch of decision point 14, then no disturbance priority is necessary and disturbance events of all priority levels may be administered. The system then generates a disturbance priority message conveying that the particular disturbance events authorized for a particular disturbance priority are permitted to be performed on the subject.

As shown in FIG. 2, after the system has determined whether the subject has been asleep for a predetermined period of time $t_p$, less than the predetermined period of time $t_p$, or is awake, the system then generates a disturbance priority message for conveying the particular disturbance events that are authorized to be performed on the subject based on the determined disturbance priority, i.e., intermediate priority events (including top priority events) for an intermediate disturbance priority, top priority events for a top disturbance priority, transition disturbance events for a transition disturbance priority, and all disturbance events if the subject is awake. The disturbance priority message is then further displayed so as to convey that information to an operator, or, in the case of a hospital setting, an attendant nurse, physician, or other hospital personnel, so that the authorized protocol can be administered on the subject.

Figure 3:
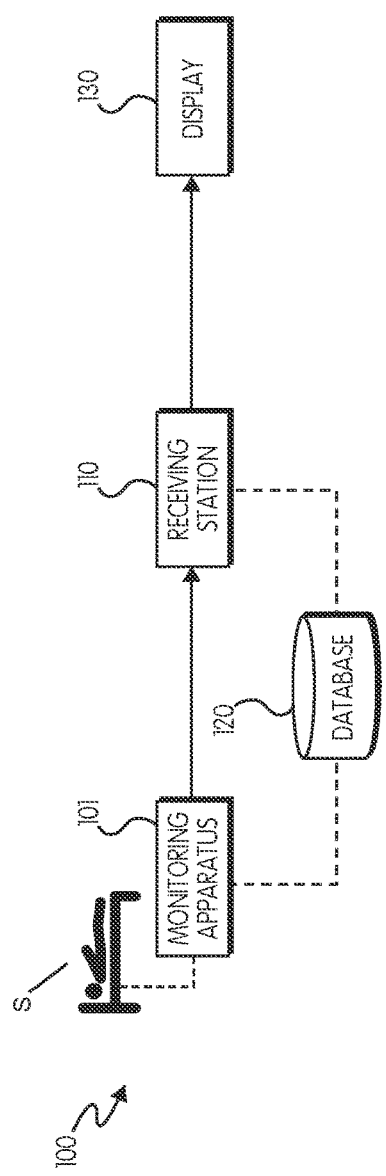
FIG. 3 is a diagrammatic representation of an embodiment of a system for preventing sleep disturbance according to the present invention.

As shown in FIG. 3, an embodiment of a system 100 according to the present invention may include a sleep status monitoring apparatus 101, a receiving station 110, and a display 130. The monitoring apparatus 101 is in communication the receiving station 110, which, in turn, in is communication with the display 130. In some embodiments, the receiving station 110 and the display 130 may be integrated into a single device or they may be separate devices, which could be located remotely from each other. The monitoring apparatus 101 is connected in some manner to a subject S. The subject S may be a patient in a hospital setting, a resident of a nursing home, a volunteer for a sleep study, or a person in any other setting wherein monitoring of sleep data may be useful. In some embodiments, the system may include an optional database 120 that is accessible by the receiving station 110 and/or the monitoring apparatus 100. The database 120 may contain rules relating to certain priority events in the system. The database 120 may be located on the receiving station 110, on the monitoring apparatus 101, or anywhere else, for example, on a server or computer on a network, that is accessible to the receiving station 110 and the monitoring apparatus 101.

Figure 4:
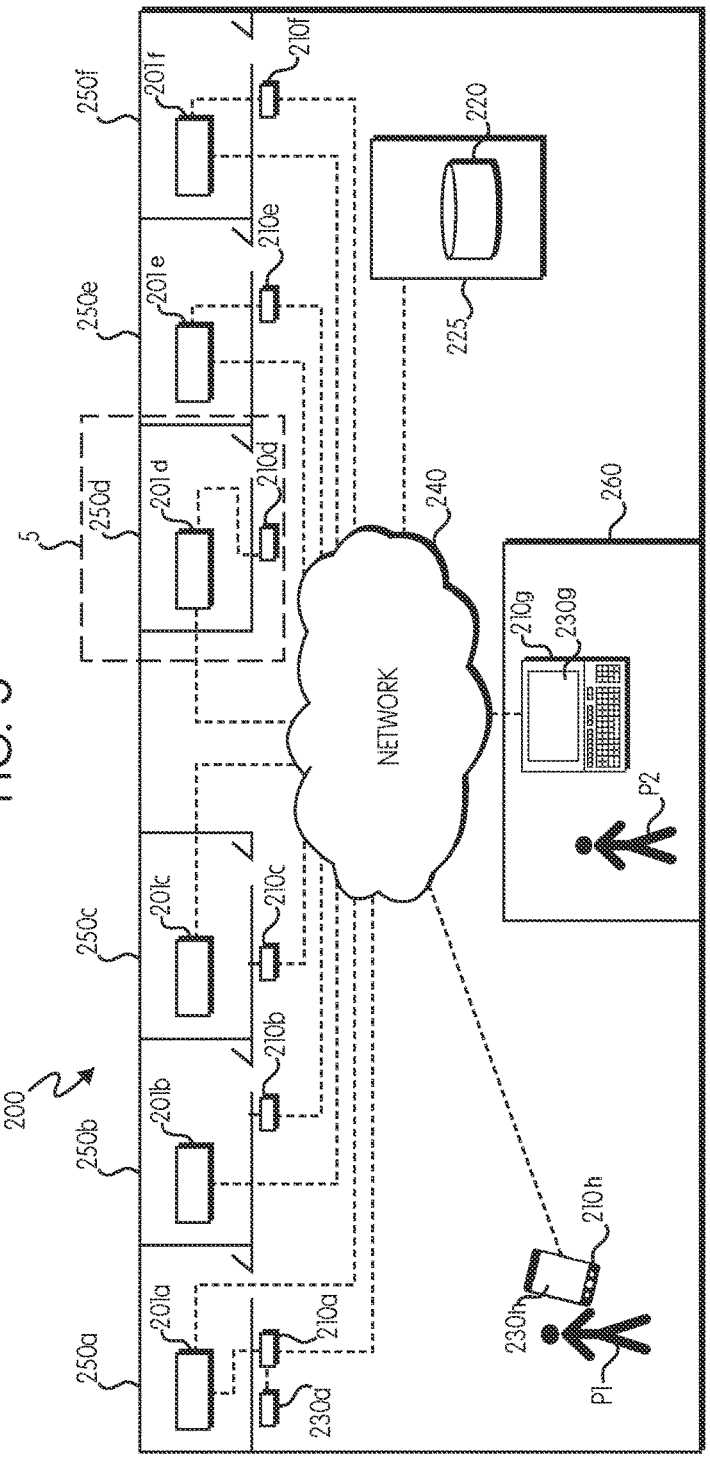
FIG. 4 is a diagrammatic representation of another embodiment of a system for preventing sleep disturbance according to the present invention.

Referring now to FIG. 4, an embodiment of a system 200 may include a plurality of sleep status monitoring apparatuses 201a-201f, a plurality of receiving stations 210a-210h, a database 220, and a network 240. In this illustration, system 200 of FIG. 4 is depicted as a portion of a hospital floor with attending medical personnel P1 and P2, but this configuration may be used in settings wherein multiple monitoring apparatuses/receiving stations are necessary. As shown, each of the monitoring apparatuses 201a-201f, receiving stations 210a-210h, and database 220 may be in communication with the network 240. In some embodiments, the monitoring apparatuses and receiving stations may be in direct communication with each other, such as shown with respect to monitoring apparatuses 201d-201f and receiving stations 210d-210f. For example, they may be connected directly through wireless communication, such as Bluetooth®, or through direct wired connection. Alternatively, in some embodiments, the monitoring apparatuses and receiving stations may be connected over the broader network 240, such as shown with respect to monitoring apparatuses 201a-201c and receiving stations 210a-210c, 210g, 210h.

As illustrated, the receiving stations 210a-210f of FIG. 4 may positioned remotely from the monitoring apparatus directly outside patient rooms 250a-250f. However, the receiving stations may also be positioned remotely to even the patient rooms 250a-250f, such as with respect to receiving stations 210g, 210h. Receiving station 210g may be located at an attendant or nurse's station 260, and may take the form of a computer having a monitor display 230g. In this regard, multiple subjects may be monitored from a single receiving station. Receiving station 210h may be a portable or mobile device, such as tablet computer, smart phone, or smart watch, having a display 230h that can accompany medical personnel P1 regardless of P1's location. As illustrated in FIG. 4, receiving stations 210b-210f do not include a separate display, as they may optionally include an integrated display, such as on a tablet computer or smart phone. Room 250a, on the other hand, shows an embodiment wherein the receiving station 210a is separate from the display 230a. In this instance, receiving station 210a may, for example be a computer or other hardware capable of receiving and processing the data transferred from the monitoring apparatus and displaying data on the display 230a. In such embodiments, receiving station 210a may be positioned inside room 250a with display 230a outside of room 250a. Or, as illustrated, both receiving station 210a and display 230a may be position directly outside of room 250a.

As further illustrated in FIG. 4, the database 220 may be connected to the various other components of the system 200 via the network 240, such by being located on a server 225 on network 240. Alternatively, the database 220 may be located on one or more of the monitoring apparatuses 201a-201f or receiving stations 210a-210h.

Figure 5:
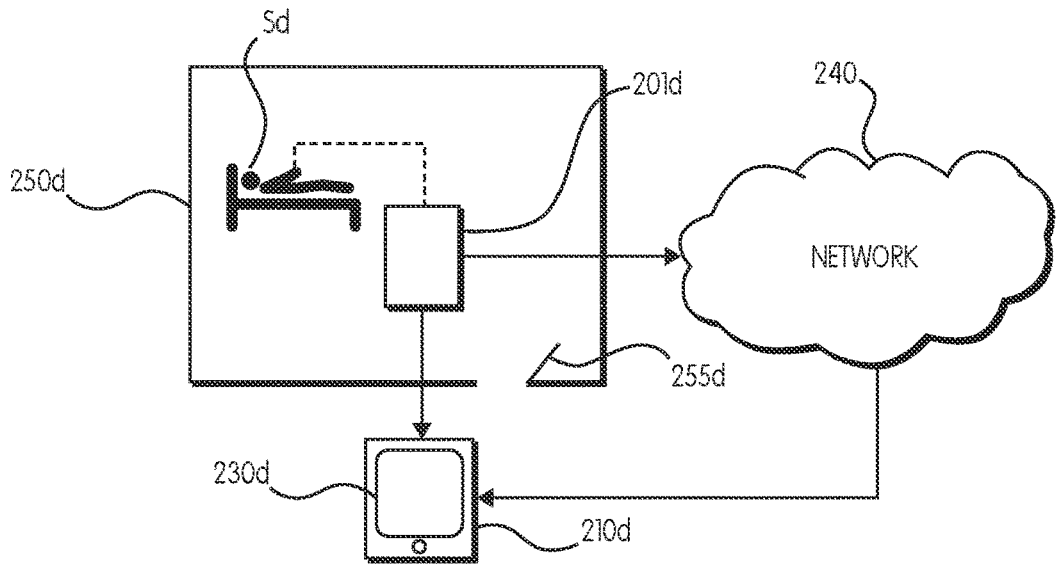
FIG. 5 is a diagrammatic representation of a detailed view of the components highlighted in box 5 of FIG. 4.

Referring now to FIG. 5, which is an enlarged view of room 250d of FIG. 4, the monitoring apparatus is connected to subject $S_d$. The monitoring apparatus 201d may take the form of an EEG monitor, such as the commercially available Z-MACHINE® from General Sleep Corporation of Euclid, Ohio or the MUSE™ from Interaxon. Of course, other techniques for monitoring the sleep of the subject $S_d$ may be utilized, such as EMG, ECG/EKG, PAT, EOG, GSR, heart monitoring, respiratory monitoring, accelerometers, or other means of measuring motion, and temperature measurement. In embodiments where the monitoring apparatus 201d takes the form of an EEG device/monitor, the apparatus measures or monitors electrical brain activity to track and/or record brain wave patterns. The monitoring apparatus 201d may take the form of electrodes placed on the head, or elsewhere, on the subject $S_d$. Alternatively, the monitoring apparatus 201d may take the form of a headband to be worn on the head of subject $S_d$, wherein the headband would include electrodes to measure electrical brain activity. The monitoring apparatus 201d is in communication with the receiving station 210d. The monitoring apparatus may be connected directly to receiving station 210d, such as through the connections explained above, or through the broader network 240. The example shown in FIG. 5 shows the receiving station 210d as having an integral display 230d. In this instance, receiving station 201d may take the form of a tablet computer, but may take the form of any hardware capable of receiving and processing the data transmitted from the monitoring apparatus and displaying data indicative of the data received.

In practice, the monitoring apparatus 201d collects real-time sleep status data from the subject $S_d$. For example, in the case where the monitoring apparatus 201d takes the form of an EEG monitoring device, the monitoring apparatus could measure and collect electrical brain activity data, or, in the case where the monitoring apparatus 201d includes accelerometer functionality, the monitoring apparatus may measure and collect movement data. The monitoring apparatus 201d also transmits the real-time sleep status data to the remotely positioned receiving station 210d via, as explained above, BLUETOOTH® or other wireless communication method, through a larger network, and/or a wired connection. The receiving station 210d, upon receiving the real-time sleep status data, may process the data according to the steps illustrated in FIGS. 1-2. Accordingly, it may determine a sleep disturbance priority based at least partially on the real-time sleep status data and may generate a sleep disturbance message including data indicative of the sleep disturbance priority level. The determination of the sleep disturbance priority may take place alternatively at the monitoring apparatus 201d as well. The receiving station may then display the sleep disturbance message on the display 230d located remotely from the sleep status monitoring apparatus 201d.

In some embodiments, the systems herein may incorporate a database, such as databases 120, 220. Referring to database 120 of FIG. 3, the database may be accessible by both the receiving station 110 and the monitoring apparatus 101. The database 120 may be located on either the receiving station 110 or the monitoring apparatus 101. Alternatively, as shown in FIG. 2, a database 220 may simply be accessible to the various components of the system via the overall network. The database may take the form a relational database. The database may include rules associated with what disturbance events may be administered. For example, the rules may include a priority ranking of disturbance events to be administered by an operator on the subject.

Figure 6:
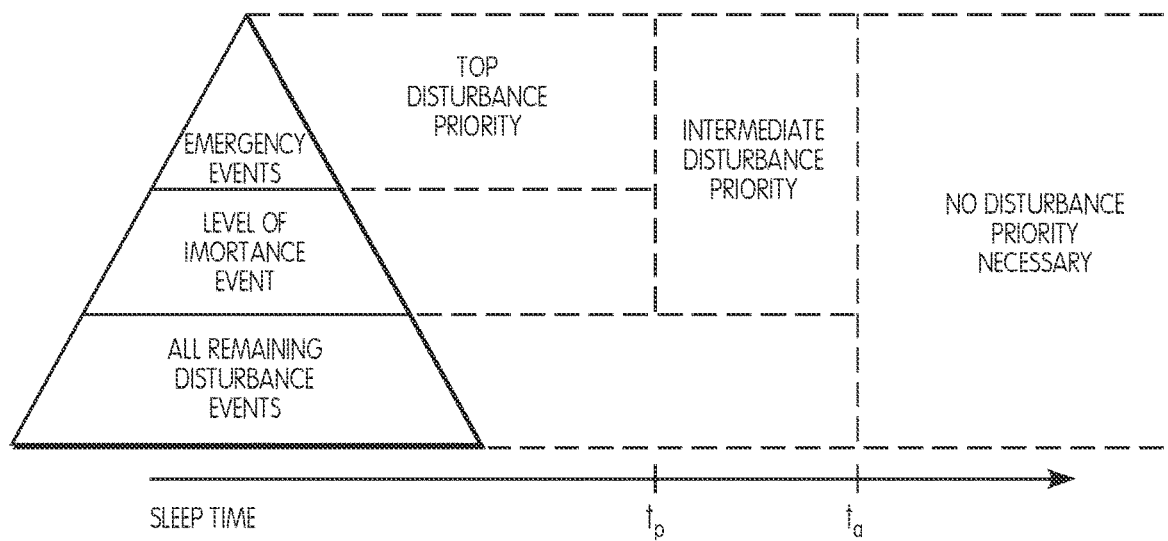
FIG. 6 is a graphical representation of an embodiment of the rules of a system for preventing sleep disturbance according to the present invention.

A graphic depiction of an exemplary embodiment of these rules is shown in FIG. 6. In FIG. 6 the horizontal axis represents sleep time. There are two points in time represented on the horizontal axis, $t_p$ and $t_a$. Time $t_p$ represents a predetermined period of time, which may be a period of sleep determined to be long enough to provide a sleep benefit to the subject. For example, $t_p$ may represent one sleep cycle, a particular stage of sleep, or any other period of time. In one embodiment, $t_p$ may be 90 minutes. After a subject falls asleep, but before time $t_p$, the rules in the database may require the system to recognize a top disturbance priority and they may restrict all disturbance events to be administered on the subject except for a small number of top priority events, which may be considered emergency events. After the time $t_p$, but before time $t_a$, which the time at which the subject is awake, the rules in the database may require the system to recognize an intermediate disturbance priority and they may permit intermediate disturbance events that are not emergency procedures, but that are important enough to justify disturbing the subject. The rules in this instance may also permit administration of the top priority events during this time period. After time $t_a$, the system may recognize no disturbance priority is necessary, and the rules may dictate as such. The rules at this stage may also specify that all disturbance events, regardless of disturbance priority designation, may be administered. The rules would permit all disturbance events that are not categorized as intermediate or top priority to be performed, in addition to the intermediate or top priority events. These other remaining events may be categorized as low priority disturbance events. The rules may dictate that those disturbance events with no priority designation or a low priority designation would never be permitted to be performed during an intermediate disturbance priority or a top disturbance priority. FIG. 6 represents the disturbance events as a pyramid with the top priority events being at the top, the intermediate in the middle, and all remaining disturbance events at the base of the pyramid. This is because the rules may be implemented in such a way so as minimize the number of top priority events that are always required to be performed on a subject regardless of the subject's level/time of sleep, whereas the intermediate priority events that are permitted may be slightly more in number, and whereas, when the subject is awake, there are no restrictions on the number of disturbance events that may be performed. Alternatively, to be implemented on a database, these rules could be implemented on the receiving stations or monitoring apparatuses separately. For example, they could be programed into an application for an operating system, a tablet computer, smart phone, or other computing software, which is saved on such computer devices' hard drives.

Alternative rules may dictate the disturbance priority and authorized disturbance priority events based not simply on time, but on the stage of sleep or sleep cycle of the patient as opposed to or in combination with the patient's sleep time. For example, the monitoring apparatus may determine the stage of sleep, e.g., the standard stages 1-4 and REM sleep, based on the sleep data, e.g., EEG data, being recorded from the subject, and then based on the disturbance events and rules in the database make a determination as to what the disturbance priority level and/or authorized disturbance events should be. Rules may also be tailored to a particular subject depending on the subject's needs. A learning loop may also be included, wherein the monitoring apparatus or the receiving station modifies the rules applied to a particular subject. For example, the system may start with a single set of rules dictating which disturbance events may be administered on set time intervals of sleep, or on particular stages of sleep. But after administering these rules, the receiving station or monitoring apparatus may determine that a subject is not responding to or responds better to a particular disturbance event during a particular stage of sleep or time interval. This determination may be accomplished through manual entry of information by an operator or by direct measurement of the subject. After acquiring this information, the system may then adjust the rules as applied to the subject to modify the disturbance priority designation of one or more disturbance events. In other examples, a system, such as system 200 of FIG. 4, having multiple nodes may implement a learning loop utilizing information gathered from one or multiple nodes so as to adjust the rules to a standard across all subjects.

Non-limiting examples of disturbance events may be as follows: vital sign measurement, patient bathing/oral hygiene, toileting, turning and positions, blood sugar testing, blood draws, VTE prophylaxis, specimen collection, oxygen administration, respiratory treatments, medication administration, IV medication administration, new patient assessment paperwork, new patient assessment MD, X-rays, intake and output, weight and/or height measurements. In some embodiments, patient assessment paperwork, X-rays, weight and/or height measurements, or intake and output, may be examples of a low priority disturbance event, whereas medication administration, turning and positions, toileting, and vital sign measurement may be examples of intermediate priority disturbance events, and whereas oxygen administration and respiratory treatments may be examples of top priority disturbance events. Any combination of procedures or events may be combined according to the needs of a particular application.

Referring now to FIG. 7, an embodiment of a system 300 according to the present invention may include a receiving station 310 and a monitoring apparatus 301 that may be wirelessly connected to one another. The monitoring apparatus 301 may take the form of an EEG monitoring device that includes EEG monitoring sensors, such as electrodes 305, which may contact the subject. In some embodiments, the electrodes 305 may be placed on the head for EEG monitoring.

Figure 8:
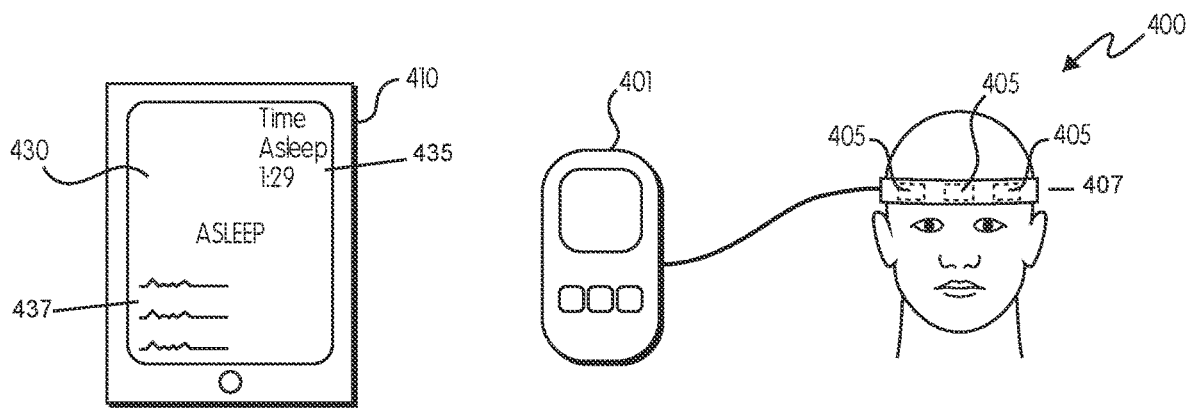
FIG. 8 is a diagrammatical representation of yet another embodiment of a system for preventing sleep disturbance according to the present invention.

As shown in FIG. 8, in another embodiment, a system 400 may include a monitoring apparatus 401 and a receiving station 410. In this embodiment, however, the monitoring apparatus 401 may include a headband 407, that incorporates electrodes 405, that is to be positioned in a noninvasive manner on the subject's head. As evident from FIGS. 7-8, the monitoring apparatus may include displays 330, 430. The displays may be configured to display the messages generated by the receiving stations and/or monitoring apparatuses.

In the embodiments of FIGS. 7-8, the displays 330, 430 may be configured such that they display a message that conveys data indicative of the subject's sleep status and the sleep disturbance priority. For example, the displays 330, 430 may include a message conveying that the subject is awake or asleep. The displays 330, 430 may also display the amount of time a subject has been asleep, such as illustrated on the areas indicated by reference lines 335, 435. Other data may also be included such as illustrated by the areas indicated by reference lines 337, 437. Examples of other data that may be included, including the disturbance events authorized for a particular patient during a particular disturbance priority, such as dictated by the rules explained herein above, the vitals of the patient, as measured, for example, by conventional means, and transmitted to the receiving stations, identifying information or other information about the subject. In some embodiments, the displays may display green to indicate that the subject is awake and that all disturbance events may be administered, and the display may likewise display red to indicate that the subject is asleep and only emergency disturbance priority events may be administered. A yellow designation on the display may also be used to indicate that intermediate priority events, as well as top level events, may be administered such as after the subject has a reached a predetermined period of sleep or stage of sleep. The display may also indicate whether the subject is transitioning to sleep.

In yet further embodiments, a non-audible alarm system may be used. In hospital settings, in particular, audible alarms, such as buzzing or beeping, are used to indicate to an operator, such as a nurse, that something needs to be addressed, such as medication needing to be replaced/refilled, vital measurements reaching prohibited limits, etc. However, a non-audible alarm system may be used wherein an operator has a mobile device, such as a smart watch, smart phone, tablet, pager, or other mobile device, that can produce a non-audible alarm. What is meant by non-audible is non-audible by the subject so as not to disturb the subject more than is necessary. For example, the mobile device may vibrate, or an audible alarm remote from the subject, such as at a nurses' station, or on a remotely located operator's mobile device may be used. In some embodiments, when an alarm event occurs in a patient's room, a central control system (e.g., a central server or a cloud based processing system) is notified (e.g., via a Bluetooth® Internet Gateway connected to the alarm producing device or other communications protocol) of the alarm event and determines which mobile device(s) should be notified of the alarm event without the alarm actually sounding in the patient's room. The mobile devices can produce a non-audible notification, such as a vibration, in response to being notified of the alarm event. In some embodiments, the mobile devices can receive and display information indicating where the alarm event is occurring, a type of the alarm event, etc., and/or request input from the individual, such as an acknowledgement that he or she has been notified of the event. In another embodiment, multiple individuals or a hierarchy of individuals can be notified of the alarm event. For example, a second individual can be notified of the alarm event if a first individual fails to provide an acknowledgement thereto within a certain time period.

Figure 9:
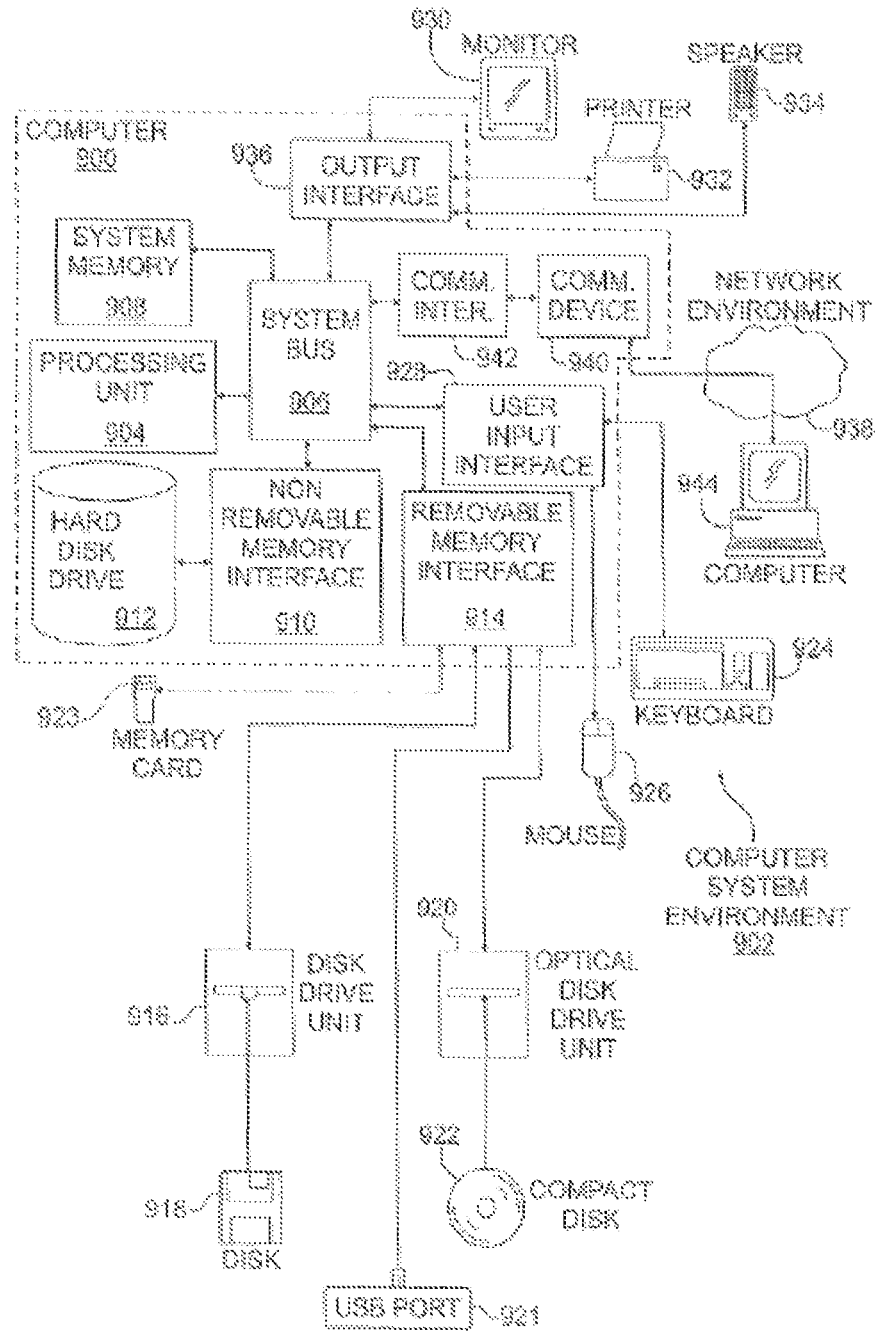
FIG. 9 is a diagrammatical representation example of system hardware on which embodiments of methods and systems according to the present invention may be implemented.

The above described embodiments, systems, and methods may be implemented on a variety of computing devices and systems, including mobile devices, such as smart phones and/or tablet computers, and/or server computers, wherein these computing devices include the appropriate processing mechanisms and computer-readable media for storing and executing computer-readable instructions, such as programming instructions, code, and the like. As shown in FIG. 9, computers 900, 944, in a computing system environment 902 are provided. This computing system environment 902 may include, but is not limited to, at least one computer 900 having certain components for appropriate operation, execution of code, and creation and communication of data. For example, the computer 900 includes a processing unit 904 (typically referred to as a central processing unit or CPU) that serves to execute computer-based instructions received in the appropriate data form and format. Further, this processing unit 904 may be in the form of multiple processors executing code in series, in parallel, or in any other manner for appropriate implementation of the computer-based instructions.

In order to facilitate appropriate data communication and processing information between the various components of the computer 900, a system bus 906 may be utilized. The system bus 906 may be any of several types of bus structures, including a memory bus or memory controller, a peripheral bus, or a local bus using any of a variety of bus architectures. In particular, the system bus 906 facilitates data and information communication between the various components (whether internal or external to the computer 900) through a variety of interfaces, as discussed hereinafter.

The computer 900 may include a variety of discrete computer-readable media components. For example, this computer-readable media may include any media that can be accessed by the computer 900, such as volatile media, non-volatile media, removable media, non-removable media, etc. As a further example, this computer-readable media may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 900. Further, this computer-readable media may include communications media, such as computer-readable instructions, data structures, program modules, or other data in other transport mechanisms and include any information delivery media, wired media (such as a wired network and a direct-wired connection), and wireless media, such as Wi-Fi and/or Bluetooth® technology. Of course, combinations of any of the above should also be included within the scope of computer-readable media.

The computer 900 further includes a system memory 908 with computer storage media in the form of volatile and non-volatile memory, such as ROM and RAM. A basic input/output system (BIOS) with appropriate computer-based routines assists in transferring information between components within the computer 900 and is normally stored in ROM. The RAM portion of the system memory 908 typically contains data and program modules that are immediately accessible to or presently being operated on by processing unit 904, e.g., an operating system, application programming interfaces, application programs, program modules, program data, and other instruction-based computer-readable codes.

With continued reference to FIG. 9, the computer 900 may also include other removable or non-removable, volatile or non-volatile computer storage media products. For example, the computer 900 may include a non-removable memory interface 910 that communicates with and controls a hard disk drive 912, i.e., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a universal serial bus (USB) port 921 for use in connection with a removable memory card, etc. However, it is envisioned that other removable or non-removable, volatile or non-volatile computer storage media can be used in the exemplary computing system environment 900, including, but not limited to, magnetic tape cassettes, DVDs, digital video tape, solid state RAM, solid state ROM, etc. These various removable or non-removable, volatile or non-volatile magnetic media are in communication with the processing unit 904 and other components of the computer 900 via the system bus 906. The drives and their associated computer storage media discussed above and illustrated in FIG. 9 provide storage of operating systems, computer-readable instructions, application programs, data structures, program modules, program data, and other instruction-based computer-readable code for the computer 900 (whether duplicative or not of this information and data in the system memory 908).

A user may enter commands, information, and data into the computer 900 through certain attachable or operable input devices, such as a keyboard 924, a mouse 926, a touchscreen, etc., via a user input interface 928. Of course, a variety of such input devices may be utilized, e.g., a microphone, a trackball, a joystick, a touchpad, a touchscreen, a scanner, etc., including any arrangement that facilitates the input of data, and information to the computer 900 from an outside source. As discussed, these and other input devices are often connected to the processing unit 904 through the user input interface 928 coupled to the system bus 906, but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the computer 900 through an output interface 936 coupled to the system bus 906. It is envisioned that any such peripheral output devices can be used to provide information and data to the user.

The computer 900 may operate in a network environment 938 through the use of a communications device 940, which is integral to the computer or remote therefrom. This communications device 940 is operable by and in communication to the other components of the computer 900 through a communications interface 942. Using such an arrangement, the computer 900 may connect with or otherwise communicate with one or more remote computers, such as a remote computer 944, which may be a personal computer, a smart phone, a tablet computer, a server, a router, a network personal computer, a peer device, or other common network nodes, and typically includes many or all of the components described above in connection with the computer 900. Using appropriate communication devices 940, e.g., a modem, a network interface or adapter, etc., the computer 900 may operate within and communicate through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers 900, 944 may be used.

As used herein, the computer 900 includes or is operable to execute appropriate custom-designed or conventional software to perform and implement the processing steps of the method and system of the present invention, thereby, forming a specialized and particular computing system. Accordingly, the presently-invented method and system may include one or more computers 900 or similar computing devices, such as smart phones, personal computers, and tablet computers, having a computer-readable storage medium capable of storing computer-readable program code or instructions that cause the processing unit 902 to execute, configure, or otherwise implement the methods, processes, and transformational data manipulations discussed hereinafter in connection with the present invention. Still further, the computer 900 may be in the form of a personal computer, a personal digital assistant, a portable computer, a laptop, a palmtop, a mobile device, a mobile telephone, a smart phone, a tablet computer, a server, or any other type of computing device having the necessary processing hardware to appropriately process data to effectively implement the presently-invented computer-implemented method and system.

Although the invention has been described herein in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A sleep monitoring and disturbance mitigation system comprising:
   a sleep status monitoring apparatus configured to collect real-time sleep data from a subject; to determine a sleep status based at least partially on the sleep data; and to transmit the real-time sleep data and sleep status to a remote receiving station; and
   a remote receiving station configured to receive the real-time sleep status data and the sleep status from the sleep status monitoring apparatus; to generate, based at least partially on the real-time sleep data and sleep status, a sleep disturbance priority and a sleep disturbance message comprising data indicative of the sleep status and the sleep disturbance priority; to display the sleep disturbance message on a display located remotely from the sleep status monitoring apparatus; and to modify a priority ranking of disturbance events based on a plurality of subjects' responses to previously administering one or more disturbance events to said subjects, each subject of the plurality of subjects being remote from one another and separately connected to a sleep status monitoring apparatus, wherein each sleep status monitoring apparatus is connected to the remote receiving station via a network.

2. The system of claim 1, wherein the sleep status monitoring apparatus is configured to wirelessly transmit the real-time sleep data and sleep status to the remote receiving station, and the remote receiving station is configured to wirelessly receive the real-time sleep status data and sleep status.

3. The system of claim 1, wherein the remote receiving station is configured to generate the sleep disturbance priority and sleep disturbance message based on at least sleep time of the subject.

4. The system of claim 3, wherein the remote receiving station is configured to generate the sleep disturbance priority based further on the priority ranking of disturbance events.

5. The system of claim 4, wherein the priority ranking comprises at least two levels of disturbance priority.

6. The system of claim 4, wherein the priority ranking comprises at least three levels of disturbance priority.

7. The system of claim 1, wherein the sleep disturbance message comprises capable of conveying at least one of the user actions of:
   (a) do not disturb the subject except for top priority disturbance events;
   (b) disturb the subject only for intermediate priority disturbance events; and
   (c) the subject is awake and all disturbance events permitted.

8. The system of claim 7, wherein the remote receiving station is configured to generate the sleep disturbance priority based at least on sleep time of the subject.

9. The system of claim 8, wherein the remote receiving station is configured to generate the sleep disturbance priority based further on the priority ranking of disturbance events.

10. The system of claim 9, wherein the priority ranking comprises at least two levels of disturbance priority.

11. The system of claim 10, wherein the priority ranking comprises at least three levels of disturbance priority.

12. The system of claim 10, further comprising an EEG monitoring sensor in communication with the sleep status monitoring apparatus, and wherein the real-time sleep data comprises EEG data, wherein the remote receiving station and the display are located on or proximate to a subject room doorway, and wherein the sleep status monitoring apparatus is configured to wirelessly transmit the real-time sleep data to the remote receiving station, and the remote receiving station is configured to wirelessly receive the real-time sleep data, the sleep disturbance message comprising data capable of conveying at least the user actions of:
   (a) do not disturb the subject except for top priority disturbance events by generating a red indicator; and
   (b) subject is awake and all disturbance events permitted by generating a green indicator.

13. The system of claim 1, wherein the remote receiving station is located on or proximate to a subject room doorway.

14. A sleep monitoring and disturbance mitigation method using a sleep status monitoring apparatus and a remote receiving station, the method comprising:
   collecting real-time sleep data from a subject at the sleep status monitoring apparatus;
   determining a sleep status;
   transmitting the real-time sleep data to the remote receiving station;
   receiving the real-time sleep data from the sleep status monitoring apparatus at the remote receiving station;
   generating based at least partially on the real-time sleep data a sleep disturbance priority and a sleep disturbance message comprising data indicative of the sleep disturbance priority; and
   displaying the sleep disturbance message on a display located remotely from the sleep status monitoring apparatus,
   wherein the remote receiving station is configured to modify a priority ranking of disturbance events based on a plurality of subjects' responses to previously administering one or more disturbance events to said subjects, each subject of the plurality of subjects being remote from one another and separately connected to a sleep status monitoring apparatus, wherein each sleep status monitoring apparatus is connected to the remote receiving station via a network.

15. The method of claim 14, wherein generating the sleep disturbance message comprises generating a message comprising data capable of conveying at least one of the user actions of:
   (a) do not disturb the subject except for top priority disturbance events;
   (b) disturb the subject only for intermediate priority disturbance events; and
   (c) the subject is awake and all disturbance events permitted.

16. The method of claim 14, wherein generating the sleep disturbance priority comprises generating the sleep disturbance priority based on at least sleep time of the subject.

17. The method of claim 16, wherein generating the sleep disturbance priority comprises generating the sleep disturbance priority based further on the priority ranking of disturbance events.

18. The method of claim 17, wherein the priority ranking comprises at least two levels of disturbance priority.

* * * * *